(12) United States Patent
Alexander

(10) Patent No.: US 8,224,458 B2
(45) Date of Patent: Jul. 17, 2012

(54) LEAD HAVING REINFORCING MEMBER

(75) Inventor: James A. Alexander, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/211,605

(22) Filed: Aug. 17, 2011

(65) Prior Publication Data

US 2011/0301678 A1  Dec. 8, 2011

Related U.S. Application Data

(62) Division of application No. 11/627,532, filed on Jan. 26, 2007, now Pat. No. 8,014,875.

(51) Int. Cl.
*A61N 1/05* (2006.01)
(52) U.S. Cl. .......................... 607/116; 607/122; 607/37
(58) Field of Classification Search .................. 607/116, 607/122, 37
See application file for complete search history.

(56) References Cited

U.S. PATENT DOCUMENTS

| | | | | |
|---|---|---|---|---|
| 5,231,996 A | * | 8/1993 | Bardy et al. | 607/126 |
| 6,119,042 A | * | 9/2000 | Verness et al. | 607/122 |
| 2005/0177199 A1 | * | 8/2005 | Hansen et al. | 607/37 |

OTHER PUBLICATIONS

MatWeb Material Property Data, "Latrobe MP35N(R) Alloy," accessed Nov. 15, 2011, <http://www.matweb.com/search/datasheet.aspx?matguid=df5edf718d6a42dbbd48ec80283d3cb2&ckck=1>, entire document.*

* cited by examiner

*Primary Examiner* — Michael Kahelin

(57) ABSTRACT

An implantable medical device, such as a lead or lead extension, includes a body having a distal end portion and a proximal end portion configured to be at least partially received by an apparatus. The device further includes a conductive member at the distal end portion of the body and an electrical contact at the proximal end portion of the body. The electrical contact is electrically coupled to the conductive member and is positioned such that, when received by the apparatus, at least a portion of the apparatus is capable of electrically coupling to the electrical contact. The device further includes a reinforcement member integrated in the body. The reinforcement member: (i) may be located in the body at a location that receives a compressive force when the proximal end portion is received by the apparatus; (ii) may be non-conductive and may be in contact with the electrical contact, and may extend distally within the body from the electrical contact; or (iii) may be located in the body at a location receivable by the apparatus.

21 Claims, 17 Drawing Sheets

LEAD HAVING REINFORCING MEMBER

PRIORITY

This patent application is a divisional of U.S. Patent Application Publication No. 2008/0183263, filed Jan. 26, 2007, now allowed, the entire contents of which are incorporated herein by reference.

FIELD

This application relates to medical devices, more particularly implantable leads and lead extensions for delivering electrical signals.

BACKGROUND

Implantable electrical signal generators, such as pacemakers, defibrillators, neurostimulators, and the like, have been used to treat a variety of diseases. Such devices generate electrical signals that are transferred to a patient's tissue through electrodes disposed on a distal end portion of a lead. The proximal end portion of a lead typically contains a number of connector rings corresponding to the number of electrodes. Conductors run within and along the lead body and electrically couple the connectors to the electrodes. The proximal end portion of the lead is inserted into connector of a signal generator such that electrical contact is made between discrete contacts in the connector portion and the connector rings of the lead. The lead is then typically secured to the connector portion of the signal generator via a set screw, which provides a compressive force on the lead, typically at one of the connector rings.

The fidelity of electrical contact between the connector portion of the implantable signal generator and the lead connector rings is important for ensuring proper electrical therapy is applied to the patient. Proper maintenance of electrical insulation of the connector rings, conductors, and electrodes is also important for ensuring proper electrical therapy is applied to the patient. However, tensile loads placed on the lead at a position distal the compressive force applied by the set screw may cause polymeric material of the lead body to pull away from the connector ring, exposing the conductors to body fluid. Accordingly, there is a need for leads having improved tensile strength to reduce the chance of the polymeric material of the lead body from separating from the connector to ensure proper function of the lead once implanted.

BRIEF SUMMARY

Leads having reinforcement members to provide improved tensile strength are described herein. In addition, other devices susceptible to exposure of conductive elements under tensile loads, such as lead extensions, having improved tensile strength are also described.

For example, an implantable medical device, such as a lead or lead extension, having a body is described. The body includes an external surface, a proximal end portion configured to be at least partially received by an apparatus, and distal end portion. The implantable medical device further includes a conductive member at the distal end portion of the body and an electrical contact at the proximal end portion of the body. The electrical contact is electrically coupled to the conductive member and is positioned such that, when received by the apparatus, at least a portion of the apparatus is capable of electrically coupling to the electrical contact. The implantable medical device further includes a reinforcement member integrated in the body. The reinforcement member: (i) may be located in the body at a location that receives a compressive force when the proximal end portion is received by the apparatus; (ii) may be non-conductive and may be in contact with the electrical contact, and may extend distally within the body from the electrical contact; or (iii) may be located in the body at a location receivable by the apparatus.

By incorporating a reinforcement member into the body of the lead, according to various embodiments disclosed herein, the load on the polymeric material of the lead body may be transferred to the reinforcement member providing the lead body with enhanced tensile strength. In addition, a reinforcement member located at the proximal end portion of the lead may result in increased stiffness of the proximal end portion, facilitating the ability to insert the lead into the connector portion of an apparatus, such as an implantable signal generator. Further, if the reinforcement member extends distally beyond a region received by the apparatus, the reinforcement member may act as a strain relief increasing the flex life of the lead. These and other advantages will be readily understood from the following detailed descriptions when read in conjunction with the accompanying drawings.

Figure 1:
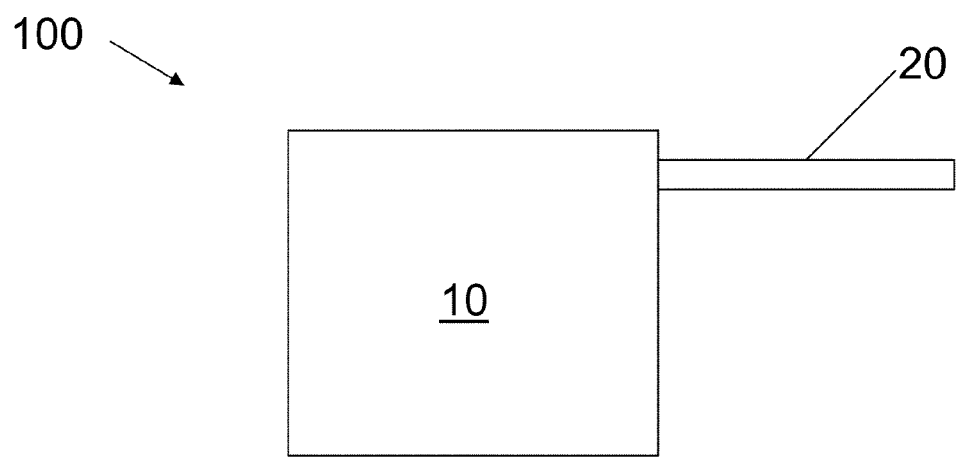
FIG. 1 is a diagrammatic representation of a side view of an implantable electrical signal therapy system.

The drawings are not necessarily to scale. Like numbers used in the figures refer to like components, steps and the like. However, it will be understood that the use of a number to refer to a component in a given figure is not intended to limit the component in another figure labeled with the same number.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "proximal" and "distal" refer to position relative to an implantable pulse generator. For example, a proximal portion of a lead is a portion nearer a signal generator, and a distal portion is a portion further from the signal generator.

As used herein, "signal generator" and "pulse generator" are used interchangeably. It will be understood that a pulse generator may generate an electrical signal or a plurality of electrical signals that are not pulses.

As used herein, "retention force", as it applies to a device, such as a lead or lead extension, relative to an apparatus, such as a pulse generator, into which the device is received, means the amount of force to cause the device to slip relative to the apparatus. It will be understood that, as used herein, terms such as "lumen", "rod", and the like may be cylindrical or of nearly any other suitable shape.

As used herein, abbreviations of units will have meanings as generally understood in the art. For example, "ksi" means kilo-pounds per square inch, "kg" means kilograms, and "MPa" means mega pascal.

The present disclosure relates to implantable medical devices, such as leads and lead extensions, comprising reinforcement members integrated into the body of the device. The reinforcement members are positioned to increase the tensile strength of the lead at a location where the body material might otherwise be susceptible to pulling away to expose conductors connecting electrical contacts to conductive members, such as electrodes. For example, the reinforcement member may be positioned at a location to be received by an apparatus, such as a pulse generator. In an embodiment, the reinforcement member is positioned in the body at a location that receives a compressive force when the proximal end portion of the device is received by an apparatus, such as an implantable pulse generator. A set screw may apply the compressive force, e.g., to an electrical contact, such as a connector ring. In an embodiment, the reinforcement member is in contact with the electrical contact. In such an embodiment, it is preferable that the reinforcement member be non-conductive.

Exemplary Systems

Figure 2:
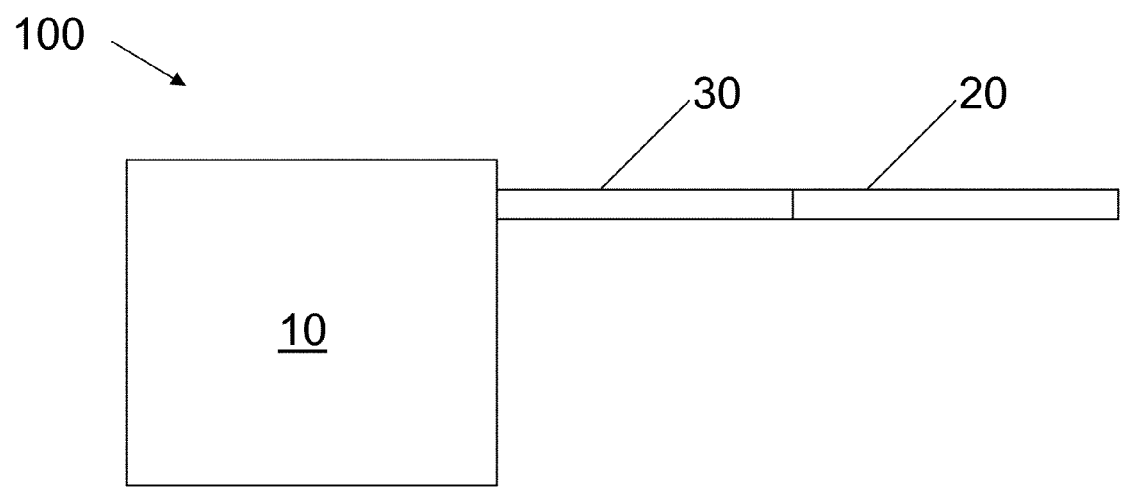
FIG. 2 is a diagrammatic representation of a side view of an implantable electrical signal therapy system.

Referring to FIG. 1, a diagrammatic representation of an implantable electrical signal therapy system 100 is shown. The system 100 comprises an implantable active electrical device 10, and a lead 20 operable coupled to active electrical device 10. Active electrical device 10 may be any electrical signal generator or receiver useful for delivering therapy to a patient or for patient diagnostics. For example, active electrical device 10 may be a hearing implant; a cochlear implant; a sensing device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like. As shown in FIG. 2, system 100 may comprise a lead extension 30 or other adaptor to couple lead 20 to active electrical device 10. While not shown, it will be understood that more than one lead 20 may be operably coupled to one active electrical device 10 or one extension 30 or that more than one extension 30 may be operably coupled to one active electrical device 10.

Figure 3:
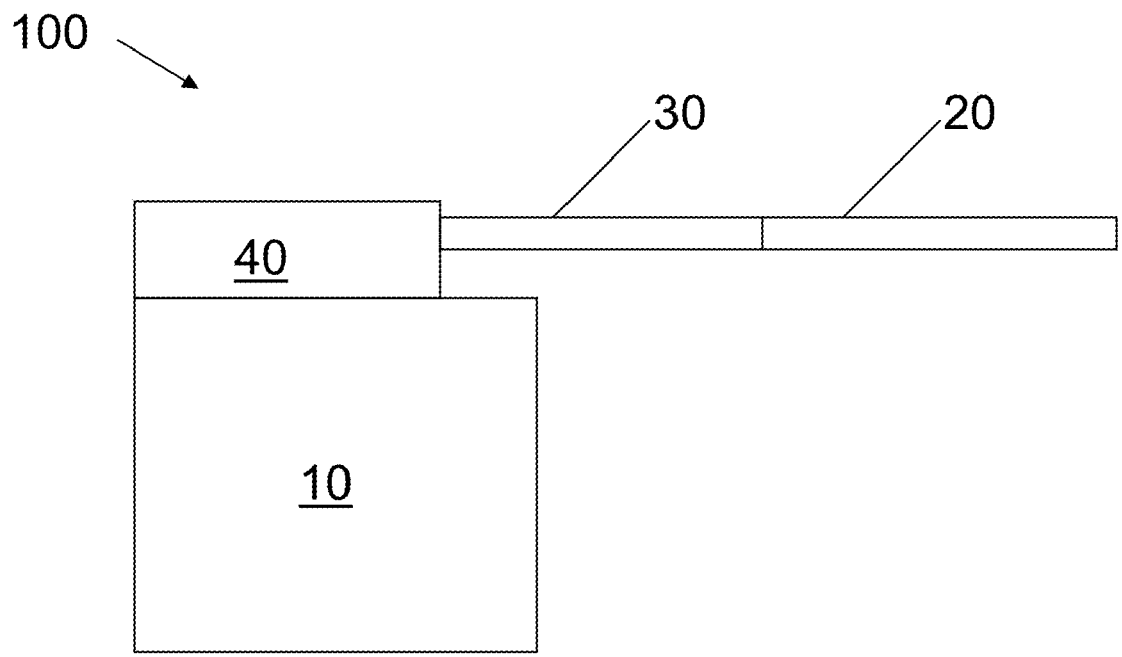
FIG. 3 is a diagrammatic representation of a side view of an implantable electrical signal therapy system.

Referring to FIG. 3, active electrical device 10 may include a connector portion 40 for connecting to lead 20 or extension 30 or other adaptor to couple lead 20 to active electrical device 10. While not shown, it will be understood that lead 20 may be coupled to active electrical device 10 without extension 30 or adaptor.

Figure 4:
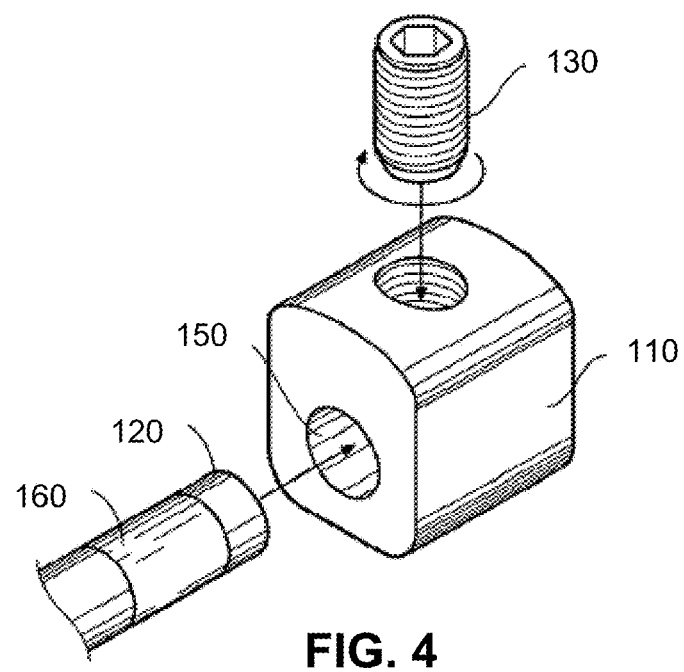
FIG. 4 is an isometric view of a portion of a connector block of a representative implantable electrical signal therapy system.

Referring to FIG. 4, an isometric view of a portion of a connector block 110 is shown. Connector block 110 may be included in connector 60 at distal end portion of extension 30 (see, e.g., FIG. 5) or connector portion 40 of active electrical device 10 (see, e.g., FIG. 3). Connector block 110 may be used to secure device 120, which may be a lead, extension, or adaptor to active electrical device, or may be used to secure lead to extension or adaptor. Device 120 may be inserted through an axially aligned opening 150 in connector block 110. The connector block 110 shown in FIG. 4 comprises a set screw 130, which may be tightened to apply a compressive force on device 120 to assist in securing device 130 relative to connector block 110, and thus relative to active electrical device 10, extension 30 or adaptor, as the case may be. It will be understood that other suitable methods, including other means for applying compressive force, for securing device 120 relative to connector block 110 may be employed. Set screw 130 may be used to electrically couple device 120 to connector block 110, and thus to active electrical device, extension or adaptor (as the case may be), by contacting electrical contact 160 of device 120. While not shown, it will be appreciated that connector block 110 may comprise a plurality of set screws along is length, which may be configured to align with and contact a plurality of electrical contacts 160 of device 120, or that active device, extension, or adaptor, as the case may be, may include a plurality of connector blocks 110.

Compressive force applied to device 120 relative to connector block 110 may be any amount of force to prevent device 120 from pulling out of connector block 110 under implanted conditions. Typically, set screws 130 are tightened with a torque wrench set at a range of 3 to 10 inch ounces (2 to 7 newton centimeter) to obtain retention force of 3 pounds (1.3 kg) or greater, e.g. 3.5 to 5 lbs (1.5 to 2.2 kg). In various embodiments, connector block 110 comprises collapsed springs, such as balseal rings (not shown), or other elastomeric material (not shown) to provide compressive force, typically at a contact 160. Such means of compressive force typically provides a cumulative retention force of 0.5 pounds (0.2 kg) or less. Such a force is typically not sufficient to retain device 120 within connector block 110 in use when implanted. Accordingly, a compressive force resulting in a retention force of 1.5 pounds (0.7 kg) or greater is desirable to retain device 120 within apparatus. In various embodiments, a compressive force that results in a retention force of 2 pounds (0.9 kg) or greater, 2.5 pounds (1.1 kg) or greater, 3 pounds (1.3 kg) or greater, 3.5 pounds (1.5 kg) or greater, 4 pounds (1.8 kg) or greater, 4.5 pounds (2 kg) or greater, or 5 pounds (2.2 kg) or greater is applied to an area of device 120 to prevent device 120 from separating from an apparatus under implant conditions.

Figure 5:
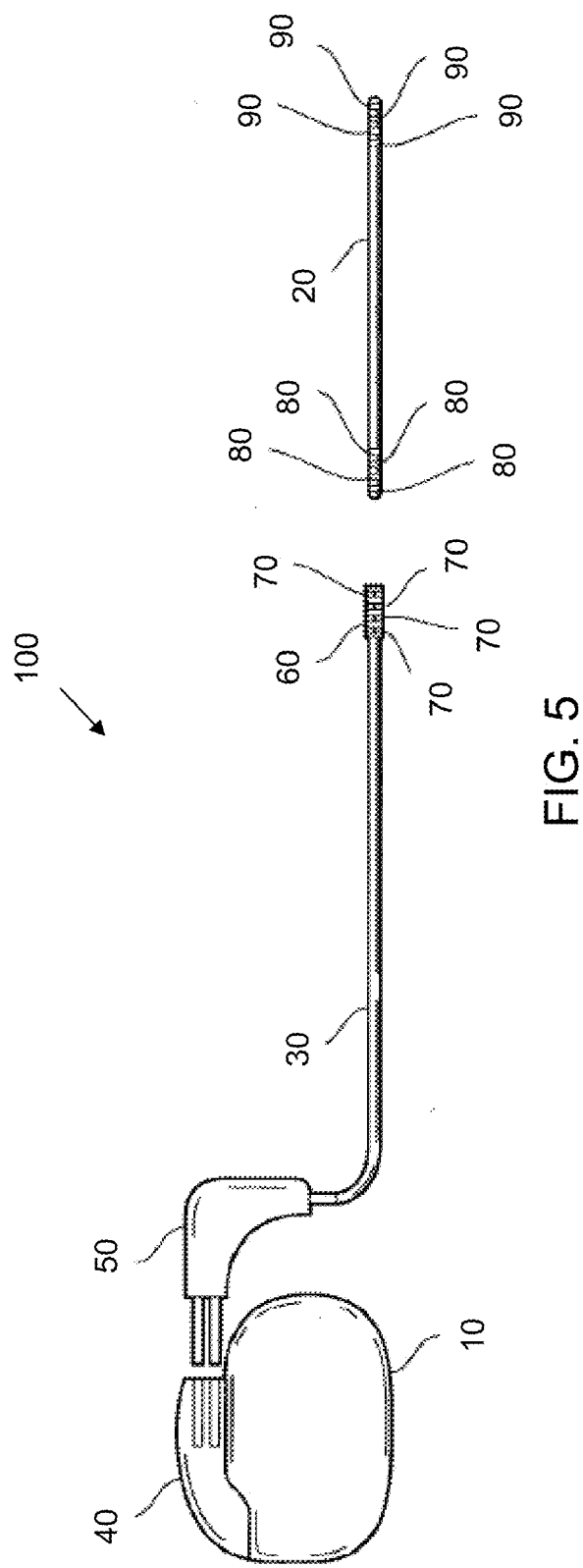
FIG. 5 is an exploded view of a representative implantable electrical signal therapy system.

Referring to FIG. 5, an exploded view of a representative implantable active electrical system 100 is shown. In the system shown in FIG. 5, implantable active electrical device 10 comprises a connector block 40 configured to receive connector 50 at proximal end of extension 30. The distal end of extension 30 comprises a connector 60 configured to receive proximal end of lead 20. Connector 60 comprises internal electrical contacts 70 configured to electrically couple extension 30 to lead 20 via electrical contacts 80 disposed on the proximal end portion of lead 20. Electrodes 90 are disposed on distal end portion of lead 20 and are electrically coupled to electrical contacts 80, typically through conductors (not shown). Lead 20 may include any number of electrodes 90, e.g. one, two, three, four, five, six, seven, eight, sixteen, thirty-two, or sixty-four. Typically, each electrode 90 is electrically coupled to a discrete electrical contact 80.

Figure 6:
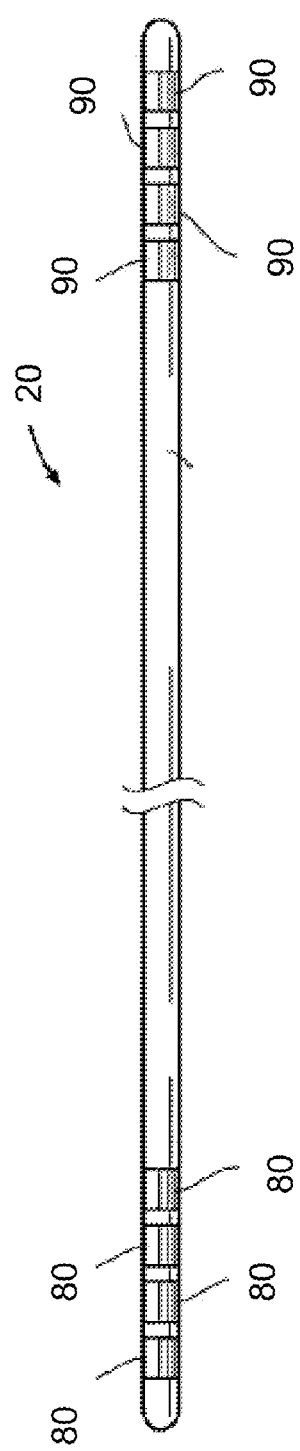
FIG. 6 is a perspective view of a representative lead.
Figure 7:
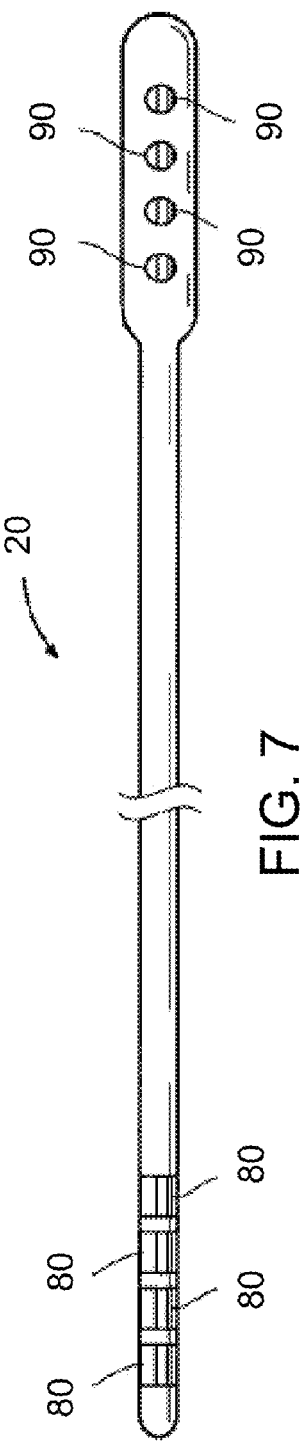
FIG. 7 is a perspective view of a representative lead.

FIGS. 6 and 7 are perspective views of representative leads 20. Leads 20, as shown in FIGS. 6 and 7, contain four exposed electrical contacts 80 and four electrodes 90. The lead 20 shown in FIG. 7 is a paddle-type lead. However, it will be understood that any lead configuration may be employed in accordance with the teachings provided herein.

Figure 8:
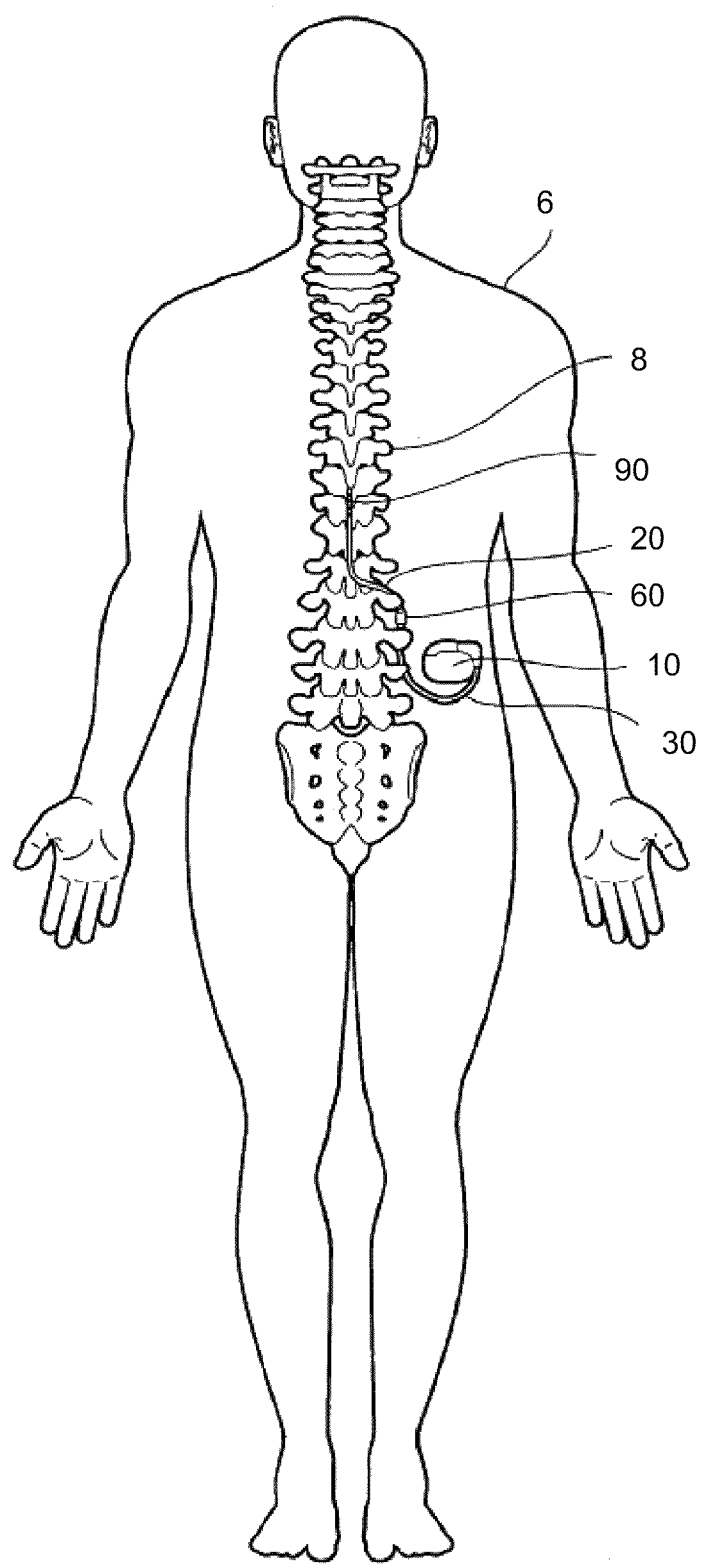
FIG. 8 is a diagrammatic representation of a representative spinal cord stimulation (SCS) system implanted in a patient.

By way of example and referring to FIG. 8, a spinal cord stimulation (SCS) system, is shown implanted in a patient 6. For SCS, an implantable pulse generator (IPG) 10 is typically placed in the abdominal region of patient 6 and lead 20 is placed at a desired location along spinal cord 8. Such a system, or any system including an IPG 10 as described herein, may also include a programmer (not shown), such as a physician programmer or a patient programmer. IPG 10 is capable of generating electrical signals that may be applied to tissue of patient 6 via electrodes 90 for therapeutic or diagnostic purposes. IPG 10 contains a power source and electronics for sending electrical signals to the spinal cord 8 via electrodes 90 to provide a desired therapeutic effect. It will be appreciated that other systems employing active electrical devices and therapeutic uses thereof are contemplated.

Figure 9:
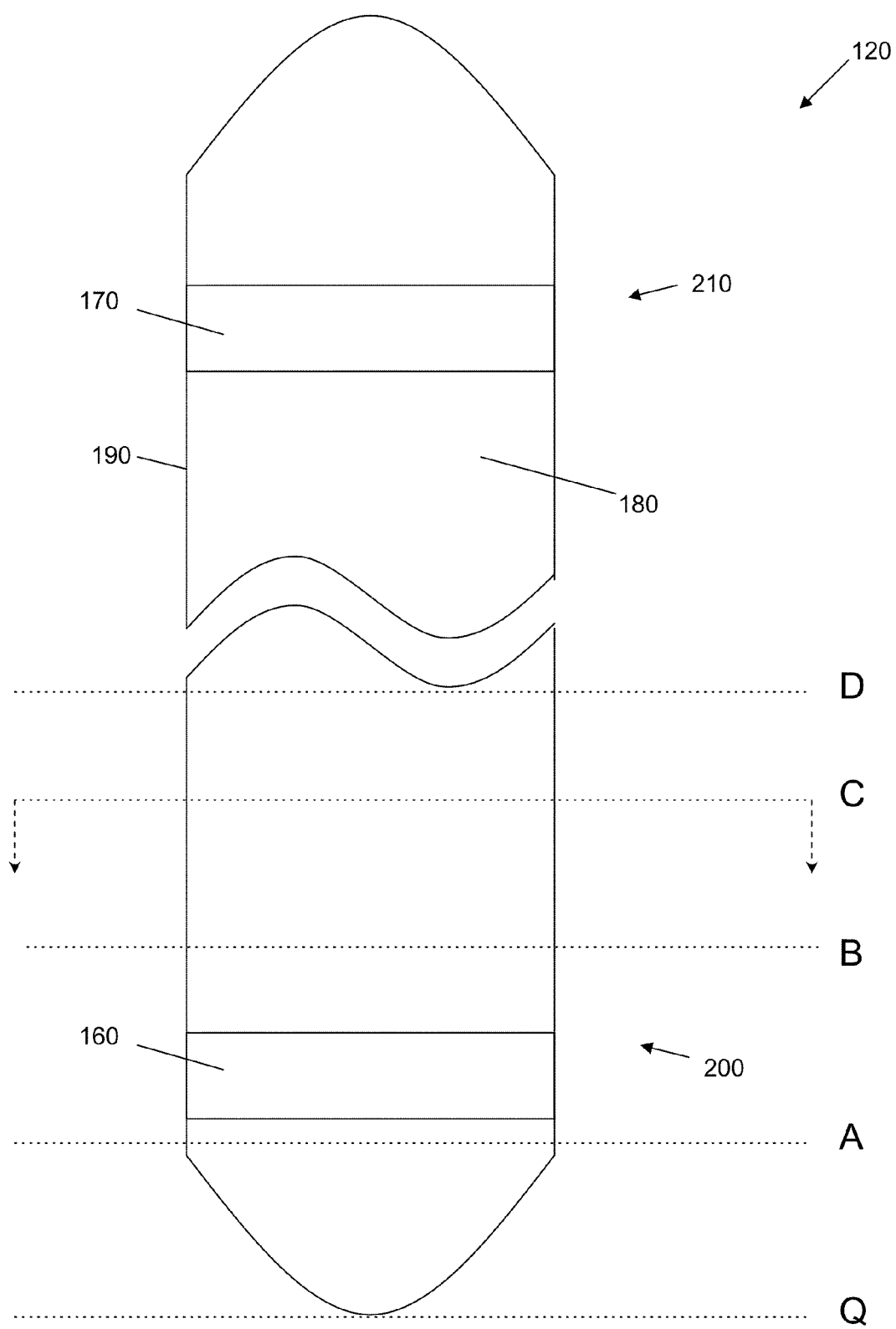
FIG. 9 is a diagrammatic representation of a top view of a representative lead.

Referring to FIG. 9, a diagrammatic representation of a perspective view of a device 120 shown. Device 120 comprises a body 180, which comprises an external surface 190, a proximal end portion 200 configured to be at least partially received by an apparatus, and a distal end portion 210. In FIG. 9, the portion of the device 120 to be at least partially received by the apparatus is shown as the portion of device 120 between lines B and Q. However, it will be understood that the portion of device 120 to be received by the apparatus may vary depending on the interaction between device 120 and apparatus. Device 120 may be a lead, extension, or adaptor configured to couple an active medical device to a lead or extension. The apparatus may be an active medical device, extension or adaptor. Device 120 includes an electrical contact 160 and a conductive member 170 electrically coupled to the electrical contact 160. Conductive member 170 may be an electrode, e.g. if device 120 is a lead, or may be a contact, e.g. if device 120 is an extension or adaptor. While not shown, it will be appreciated that device 120 may comprise a plurality of contacts 160 and conductive members 170. As shown in FIGS. 10-19, device 120 further includes a reinforcement member integrated in the body.

Figure 10:
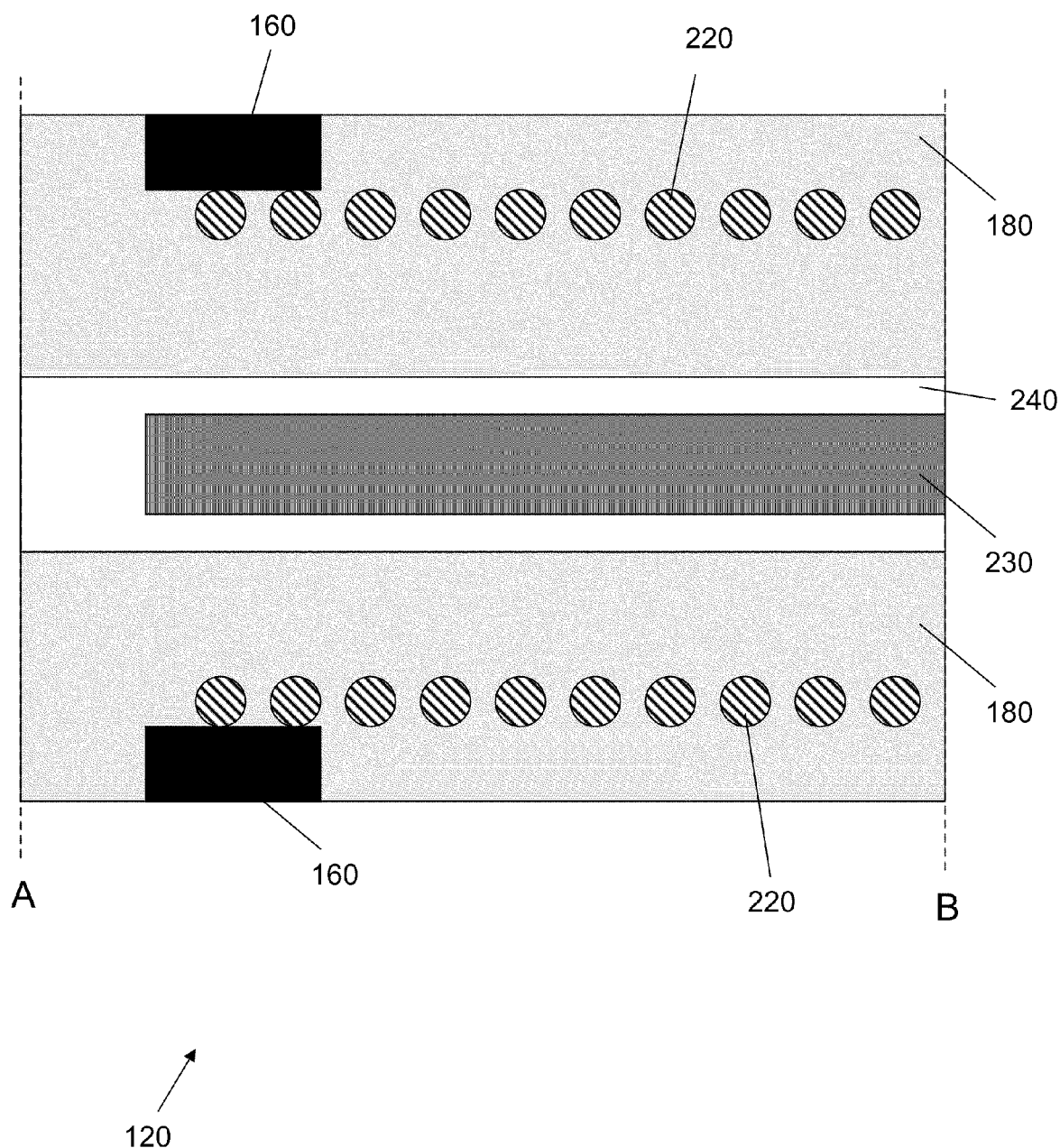
FIGS. 10 and 10A is a diagrammatic representation of a longitudinal cross section of an embodiment of the lead shown in FIG. 9 between lines A and B.

For the sake of simplicity, FIGS. 10-19 refer to embodiments of device 120 shown in FIG. 9, which includes only one contact 160 and only one conductive member 170, and show longitudinal and cross-sectional schematics of embodiments of devices 120. However, it will be understood that device 120 may comprise any number of contacts and conductive members. In the embodiment shown in FIG. 10, reinforcement member 220 is integrated into body 180 at a location to be received by the apparatus. Reinforcement member 220, as shown in FIG. 10, is a mesh or a braid. However, it will be understood that reinforcement member may be in any suitable form capable of transferring at least some load from body 180 to reinforcement member 220. In the embodiment shown in FIG. 10, reinforcement member 220 is in contact with contact 160. Such a configuration may be desirable when a compressive force is applied to contact 160 for securing device 120 relative to apparatus (e.g., as with set screw as shown in FIG. 4). Of course, reinforcement member 220 may be in contact, directly or indirectly, with any portion of body 180 or component thereof that may be subject to a compressive force when received by an apparatus.

Reinforcement member 220 provides body 180 with improved tensile strength with minimal elongation. For example, a portion of body 180 having reinforcing member 220 integrated therein can withstand an average pull force of 2 pounds (0.9 kg) with elongation of not more one-tenth the length of the segment, with the pull force being applied at a location distal to a location of a compressive force. In various embodiments, body 180 having reinforcing member 220 integrated therein can withstand an average pull force of 2.5 pounds (1.1 kg), 3 pounds (1.4 kg), 3.5 pounds (1.6 kg), 4 pounds (1.8 kg), or greater. By "withstand" it is meant that body 180 having reinforcement member integrated 220 therein will not break or tear at such average pull forces.

In various embodiments, reinforcement member 220 is connected to contact 160. That is, reinforcement member 220 may be affixed to, fastened to, adhered to, bonded to, captured or secured to or by, or otherwise attached to contact 160. In various embodiments, reinforcement member 220 is connected to contact 160 such that, when integrated into body 180, reinforcement member 220 does not separate from contact 160 when pulled with an average pull force of, for example, 2 pounds (0.9 kg) or greater, 2.5 pounds (1.1 kg) or greater, 3 pounds (1.4 kg) or greater, 3.5 pounds (1.6 kg) or greater, or 4 pounds (1.8 kg) or greater. The pull force may be applied by securing contact 160, applying a radially compressive force to body 180 at a location distal to contact 160, at which distal location reinforcement member 220 is integrated into body 180, and applying the pull force to the location of body 180 receiving the radially compressive force. The radially compressive force may be substantially uniformly applied around outer surface of body 180 at the location receiving such compressive force.

Figure 10A:
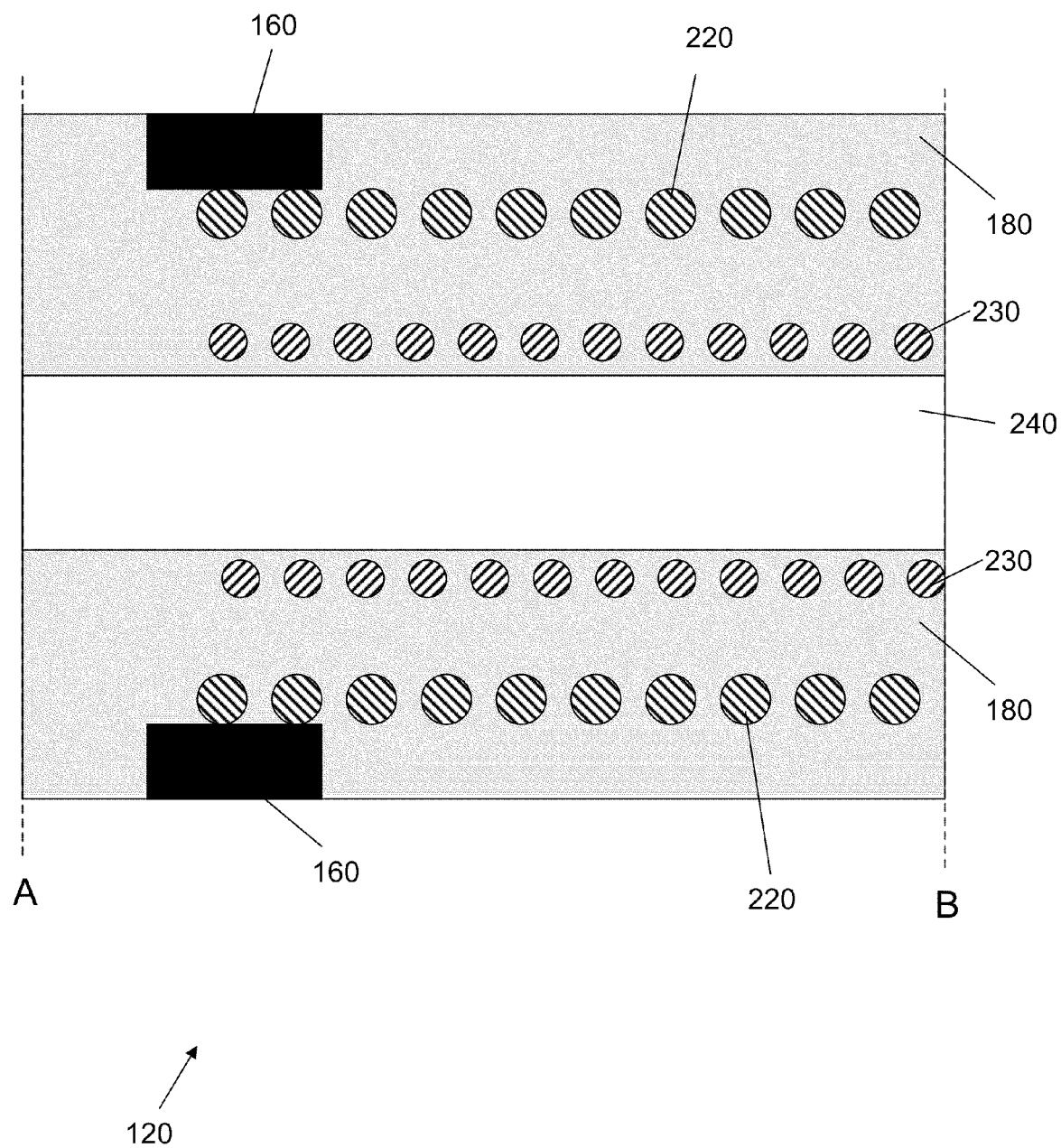

As shown in FIG. 10, device 120 may comprise a lumen 240 through which conductor 230 may be run. Of course conductor 230, which electrically couples contact 160 to conductive member 170, may be integrated into material of body 180 of device 120 (see, e.g. FIGS. 10A, 15 and 16). Further, as shown in FIG. 10A, it will be understood that conductor 230 may be spirally wound or otherwise disposed in or around lumen or in material of body 180. Of course, device 120 may have any number of lumens into which conductors, guidewires, stylets and the like may be placed. Alternatively, device 120 may have no lumen (see, e.g. FIGS. 15 and 16).

Figure 11:
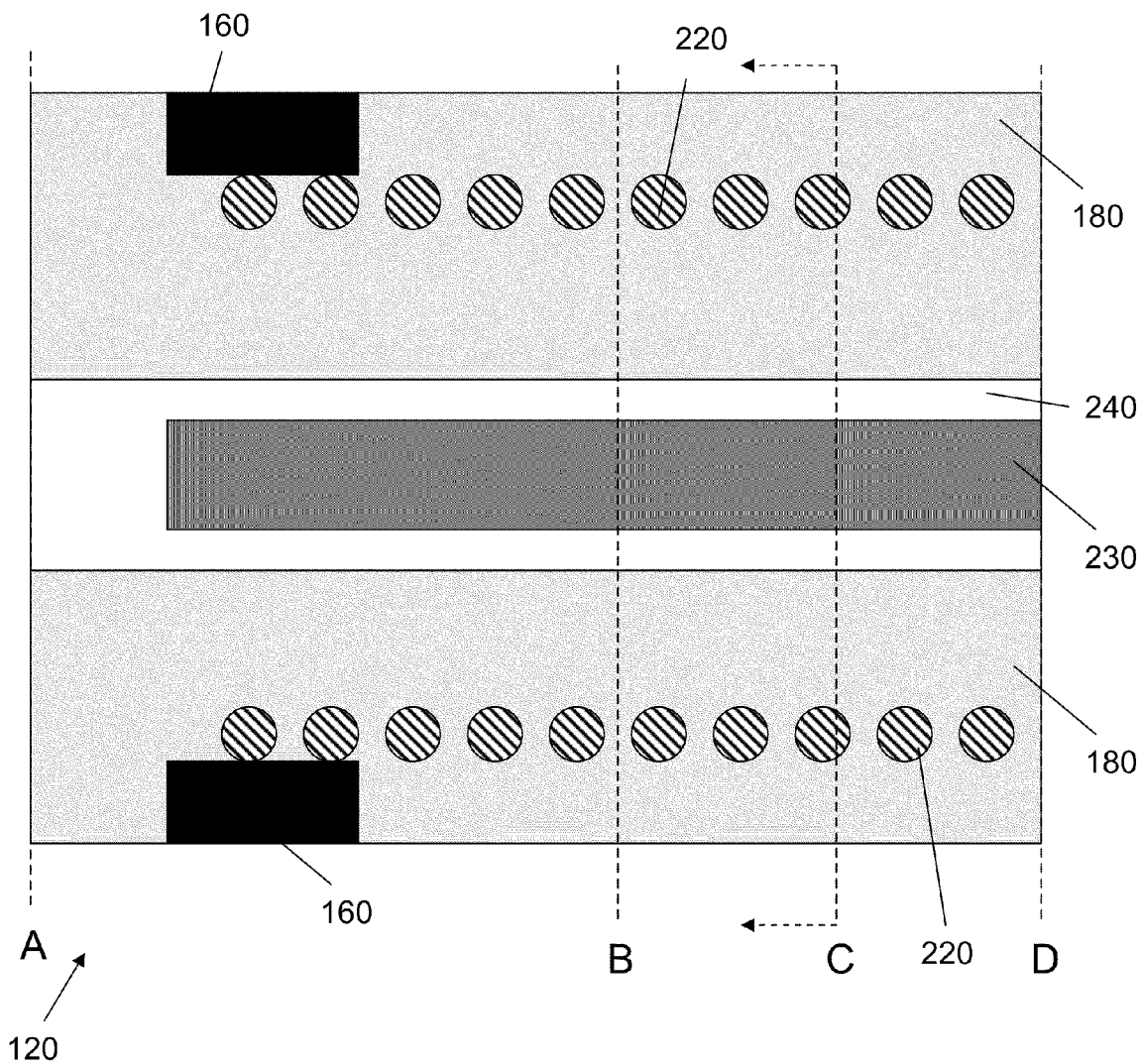
FIG. 11 is a diagrammatic representation of a longitudinal cross section of an embodiment of the lead shown in FIG. 9 between lines A and D.
Figure 12:
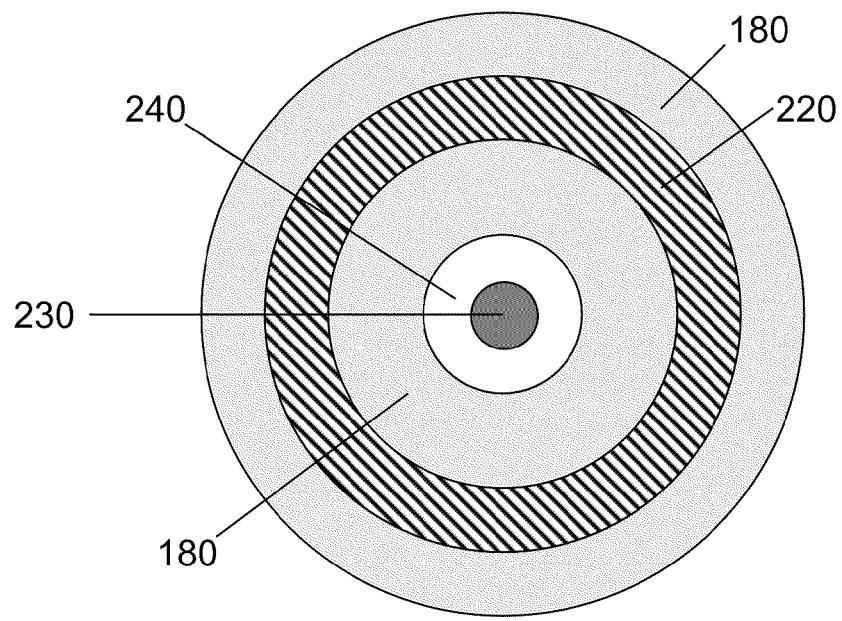
FIG. 12 is a diagrammatic representation of a radial cross section of an embodiment of the lead shown in FIG. 11 taken at line C.

As shown in the embodiment in FIG. 11, reinforcement member 220 may extend in body 180 from an area to be received by the apparatus (i.e., between lines A and B) to a location distal the area to be received by the apparatus (i.e., between lines B and D). FIG. 12 is a radial cross section taken through line C of FIG. 11, showing reinforcing member 220 integrated in material of body 180.

Figure 14:
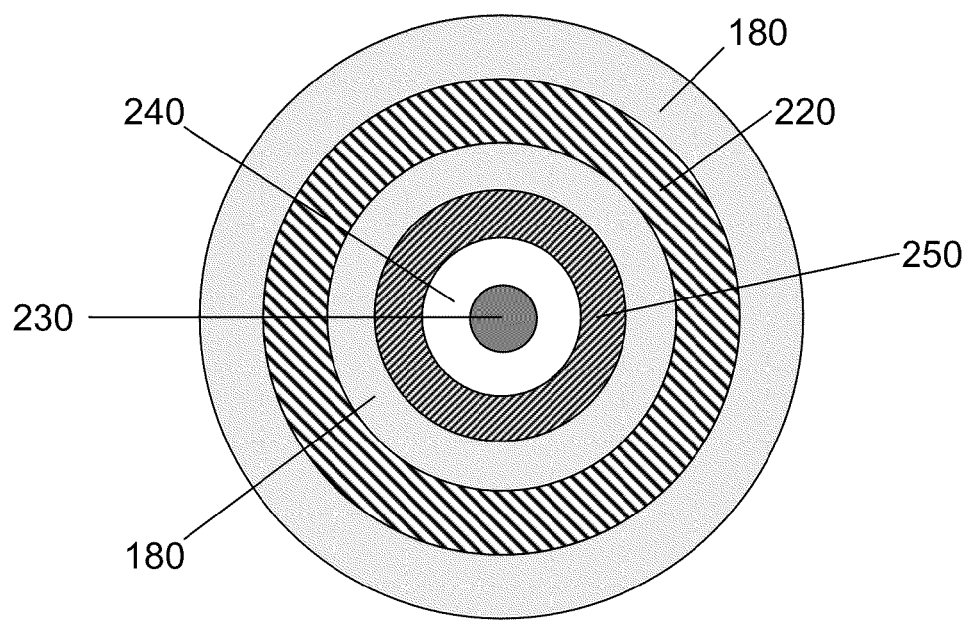
FIG. 14 is a diagrammatic representation of a radial cross section of an embodiment of the lead shown in FIG. 13 taken at line C.
Figure 13:
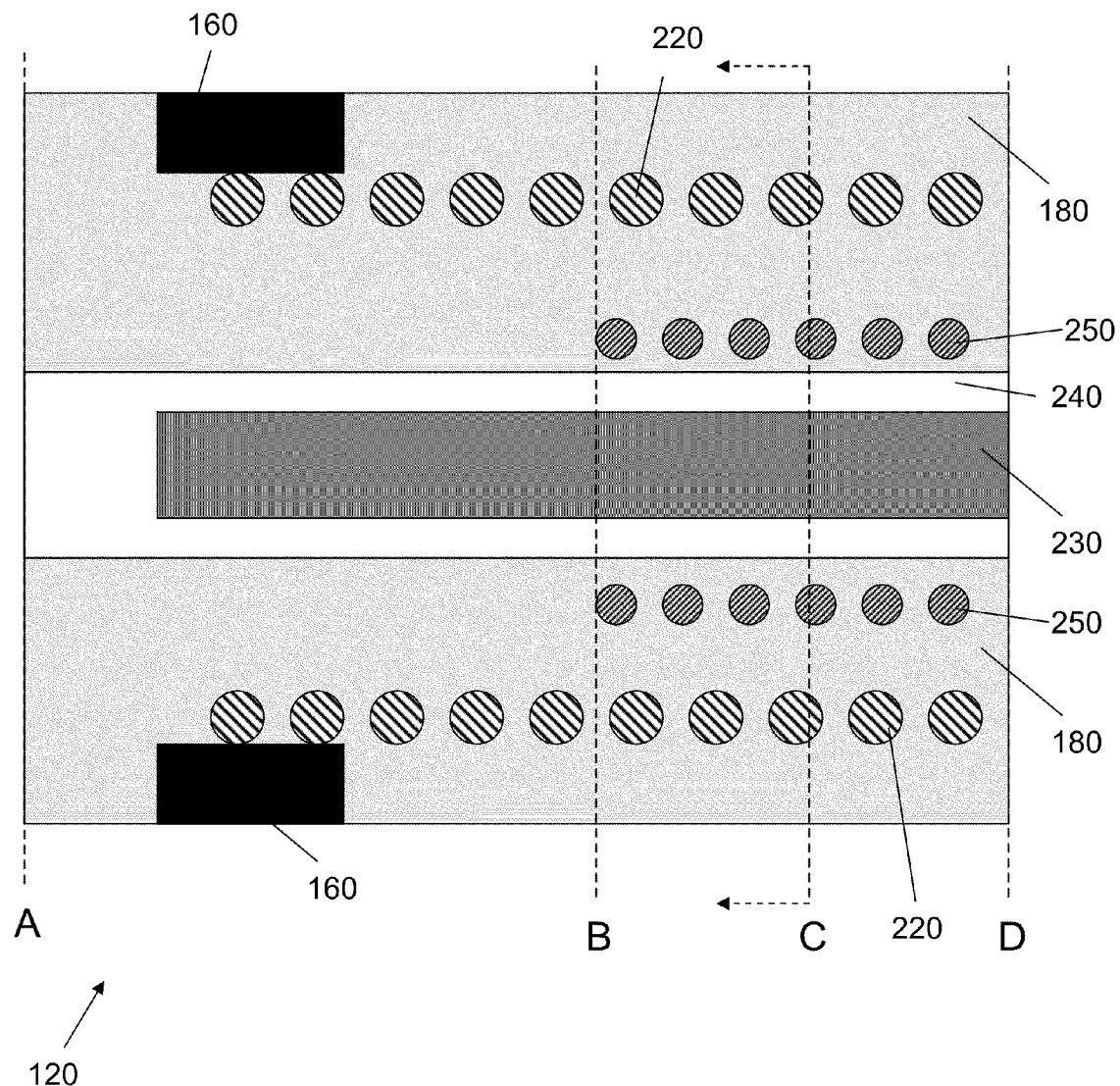
FIG. 13 is a diagrammatic representation of a longitudinal cross section of an embodiment of the lead shown in FIG. 9 between lines A and D.
Figure 15:
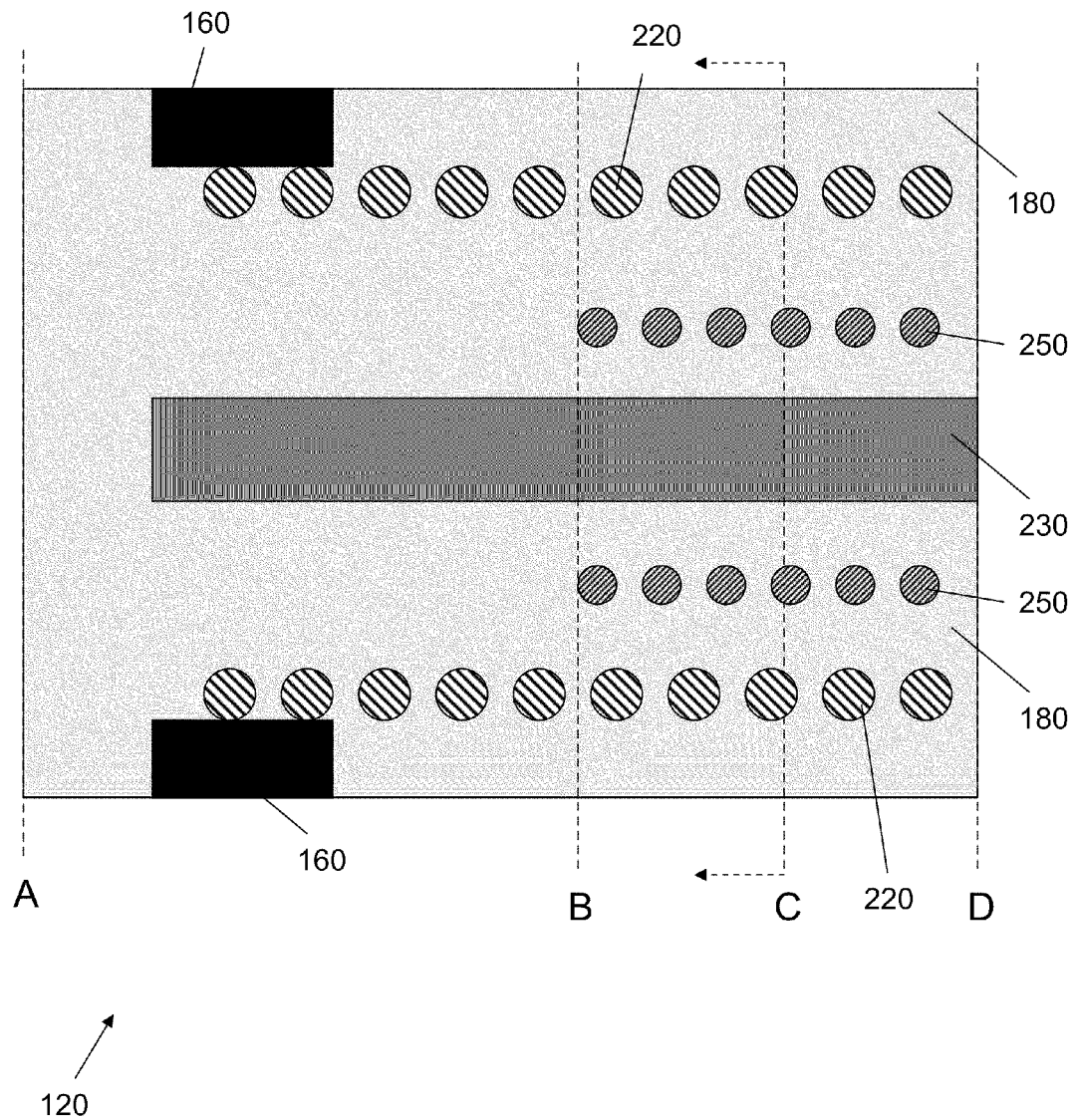
FIG. 15 is a diagrammatic representation of a longitudinal cross section of an embodiment of the lead shown in FIG. 9 between lines A and D.
Figure 16:
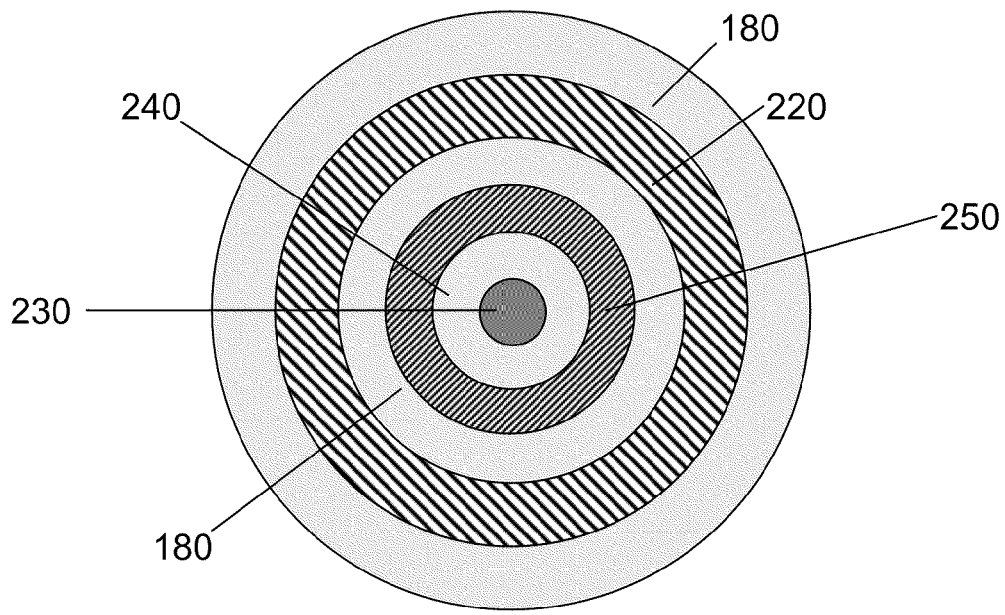
FIG. 16 is a diagrammatic representation of a radial cross section of an embodiment of the lead shown in FIG. 15 taken at line C.

Referring to FIG. 13, a longitudinal cross section of an embodiment of device 120 between lines A and D of FIG. 9 is shown. A shielding member 250, such as an MRI-safe mesh or braid, is shown. Shielding member 250 may be disposed anywhere in device 120 where it may function for its intended purpose, such as, for example, insulating at least a portion of conductor 230 from magnetic energy during magnetic resonance imaging. In an embodiment, shielding member 250 is spaced apart from conductor 230 along the length of shielding member 250. In the embodiment shown in FIG. 13, the portion of shielding member 250 between lines A and D is disposed between reinforcement member 220 and conductor 230. FIG. 14 is a radial cross section taken through line C of FIG. 13, showing shielding member 250 integrated in material of body 180 and disposed between reinforcing member 220 and conductor 230. FIGS. 15 and 16 shown an embodiment similar to FIGS. 13 and 14, but without a lumen 240. For further information on shielding members 250, and more particularly MRI-safe shielding members, see e.g., US Patent Application Publication No. 2005/0222658, entitled "Lead electrode for use in an MRI-safe implantable medical device," filed on Dec. 10, 2004, which application is hereby incorporated by reference in its entirety to the extent that it does not conflict with the disclosure presented herein.

Figure 18:
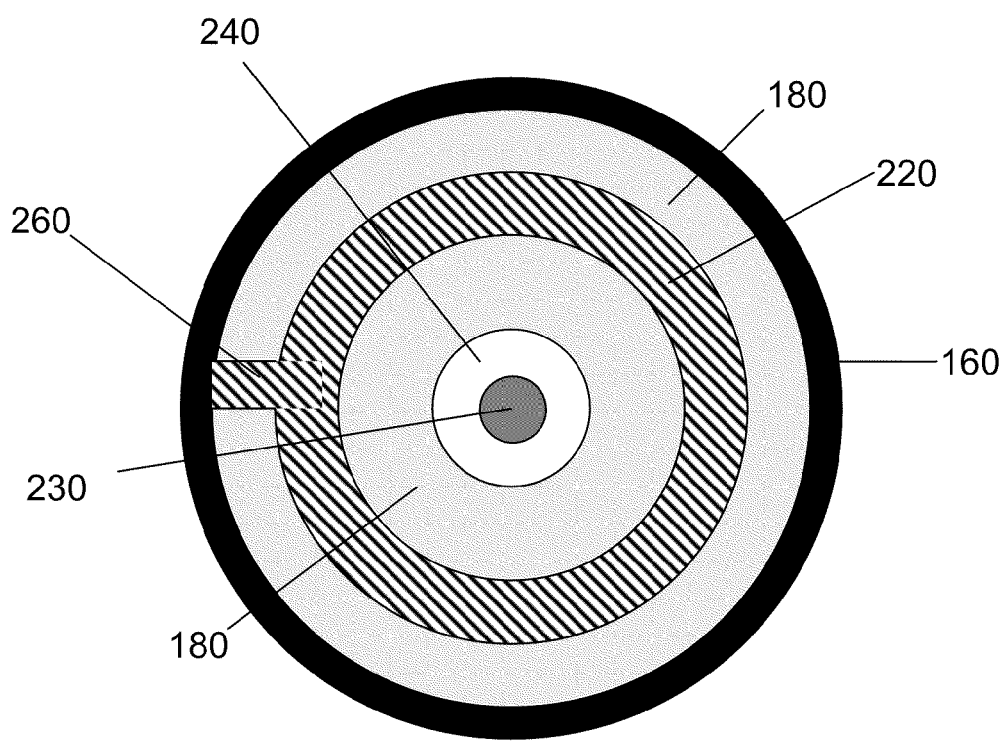
FIG. 18 is a diagrammatic representation of a radial cross section of an embodiment of the lead shown in FIG. 17 taken at line E.
Figure 17:
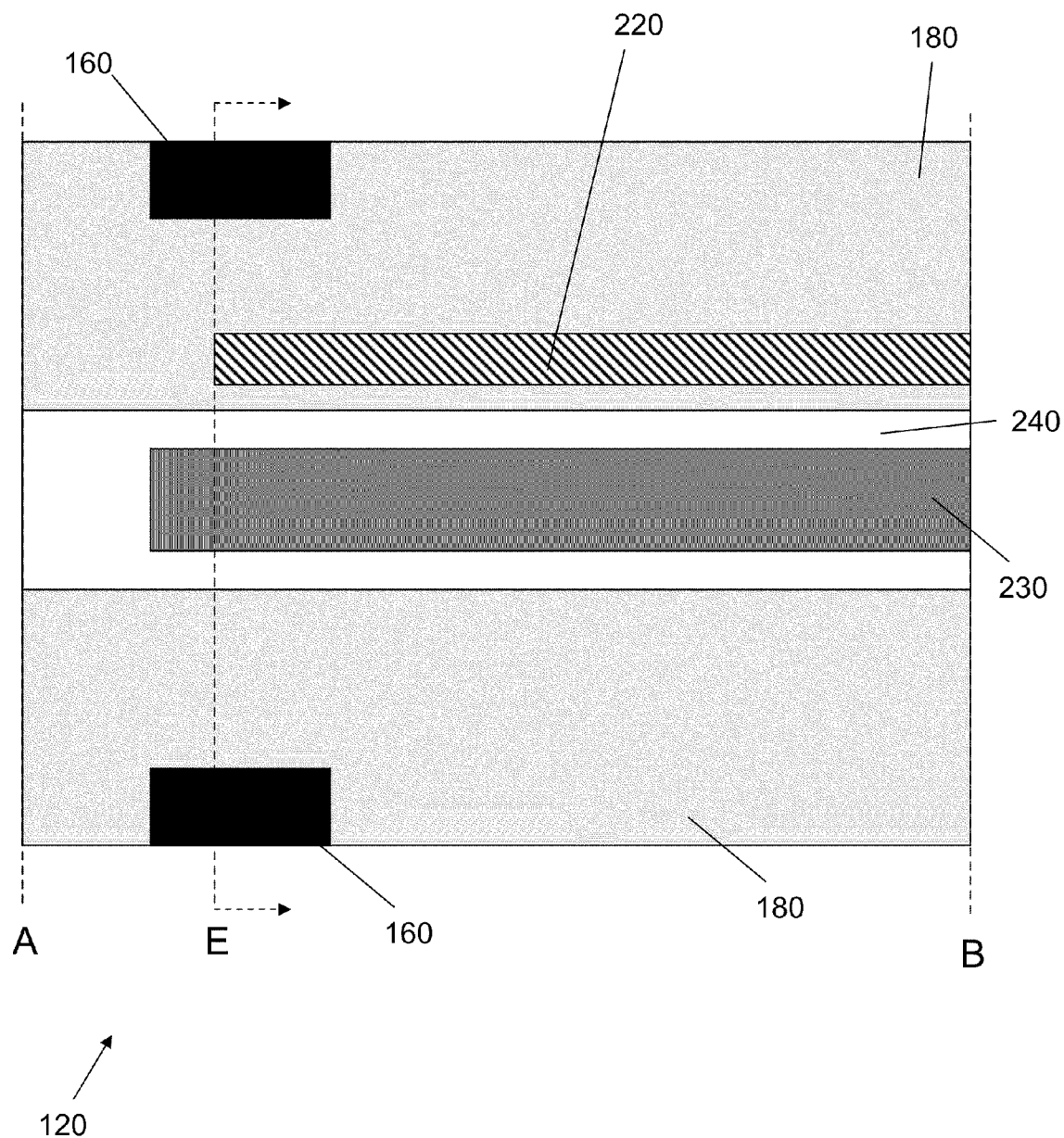
FIG. 17 is a diagrammatic representation of a longitudinal cross section of an embodiment of the lead shown in FIG. 9 between lines A and B.

FIGS. 17 and 18 show embodiments of device 120, where reinforcing member 220 is a rod. Reinforcing rod 220 is integrated into material of body 180 and is connected to contact 160 via cross bar 260 (see FIG. 18). In this embodiment, tensile load placed on device 120 as a result of a distal pulling force and a compressive force placed on connector 160 will be transferred to reinforcing rod 220.

Figure 19:
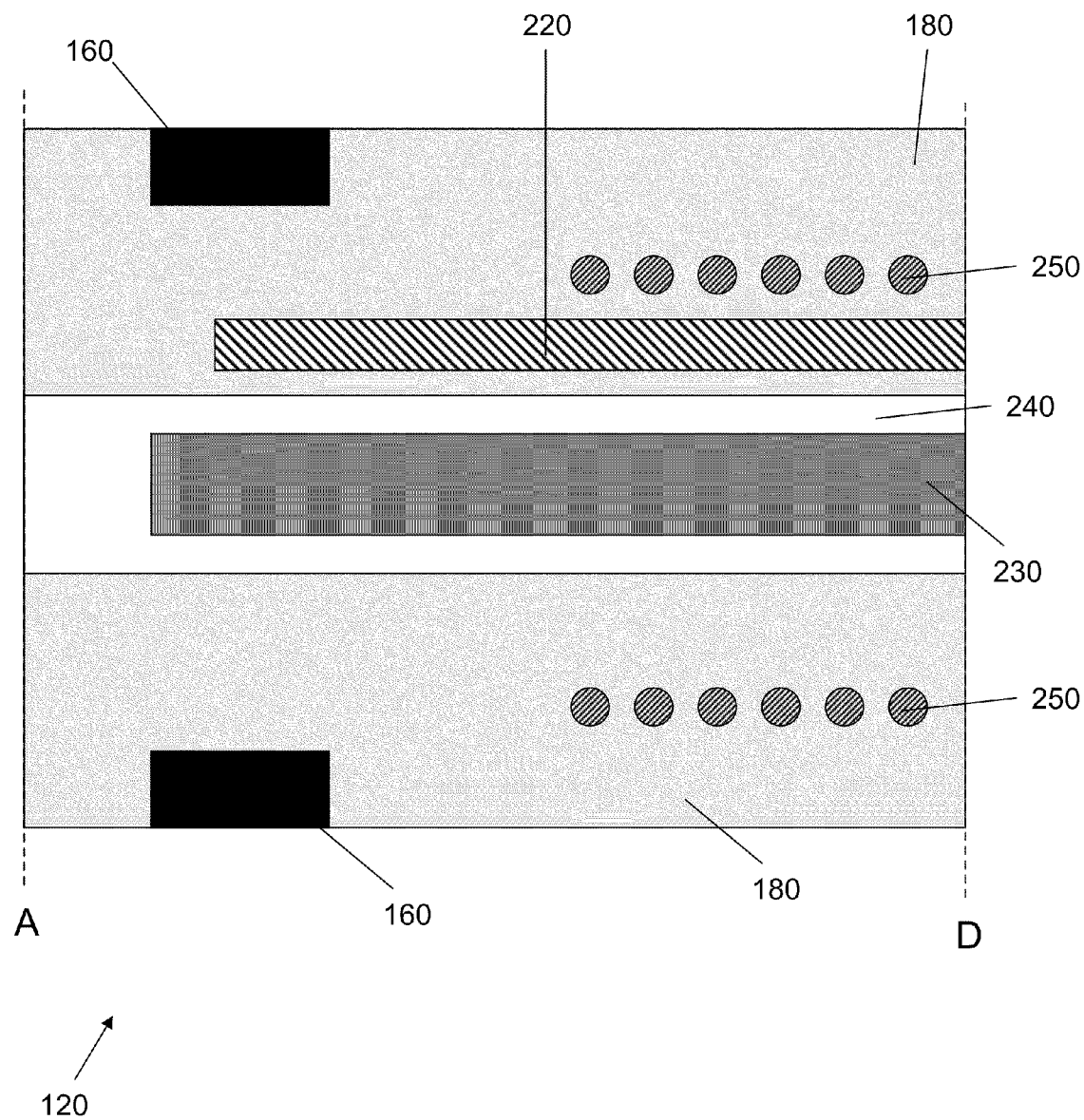
FIG. 19 is a diagrammatic representation of a longitudinal cross section of an embodiment of the lead shown in FIG. 9 between lines A and D.

FIG. 19 shows an embodiment similar to FIGS. 17 and 18, where device 120 includes a shielding member 250. In the embodiments shown in FIG. 19, reinforcing member 220, in the area shown between lines A and D, is disposed between shielding member 250 and conductor 230.

Figure 20:
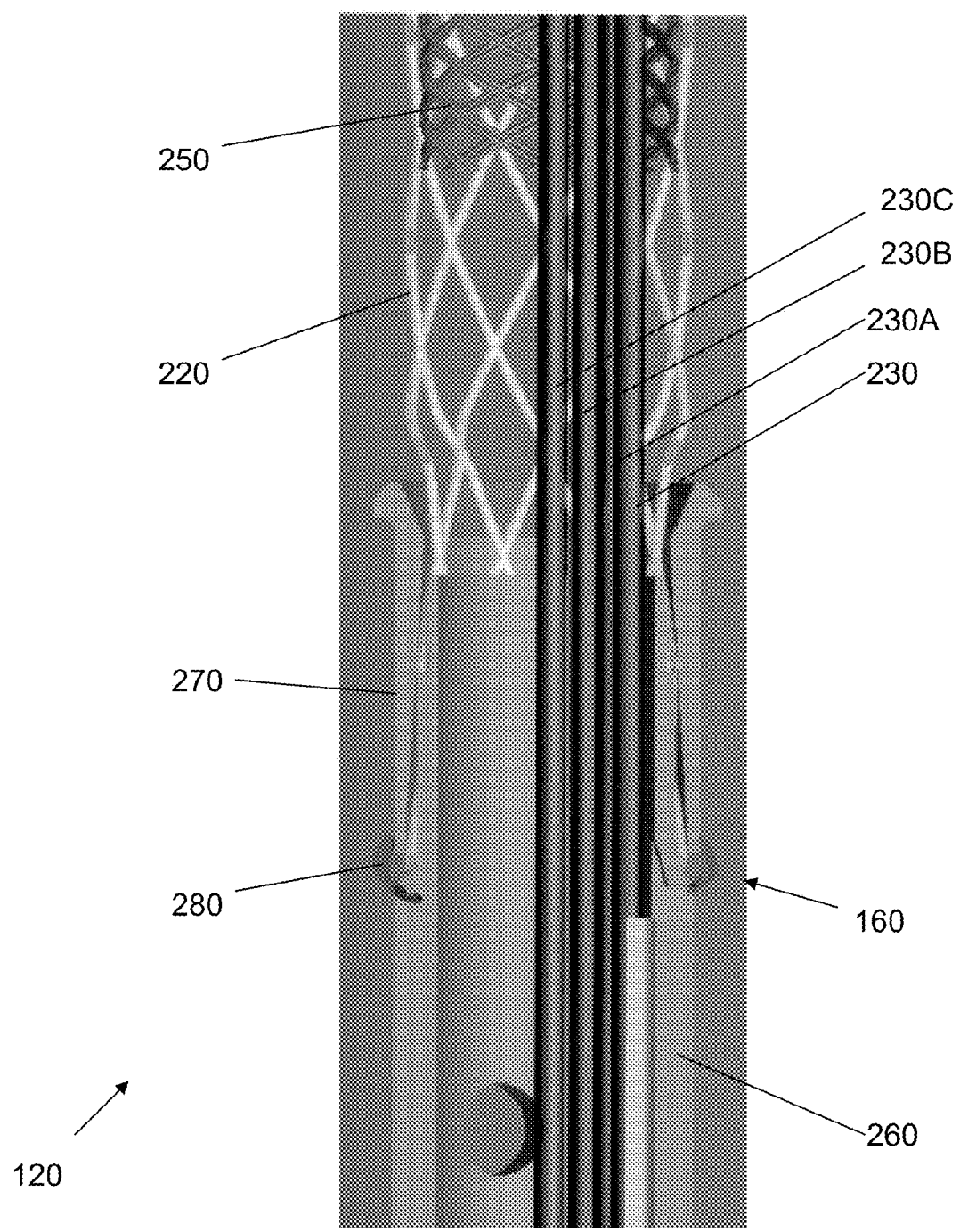
FIG. 20 is a diagrammatic representation of a cut away longitudinal cross section of a representative proximal portion of a device.

Referring to FIG. 20, a cut away longitudinal cross section of a representative proximal portion of device 120 is shown. Body material of device 120 is not shown in FIG. 20. Connector 160, as shown in the embodiment of FIG. 20, has a first part 260 having an outer surface and a second part 270 having an inner surface. At least a portion of the inner surface of the second part 270 is configured complementarily relative to at least a portion of the outer surface of the first part 260. Proximal end portion of reinforcing member 220 is disposed between the first part 260 and second part 270 of connector 160. At least a portion of the inner surface of the second part 270 comprises a lumen configured to receive the at least a portion of outer surface of the first part 260. As shown in FIG. 20, the at least a portion of the inner surface of the second part 260 comprises a conical portion comprising a proximal end and a distal end, wherein the distal end of the conical portion has a larger circumference than the proximal end of the conical portion. As further shown in FIG. 20, the at least a portion of the outer surface of the first part 260 comprises a tapered portion, where the proximal portion of the outer surface has a larger circumference than the distal portion of the tapered portion. First part 260 may be pressed to second part 270. A weld 280 may be used to ensure electrical coupling of first part 260 to second part 270 of connector 160.

Figure 21:
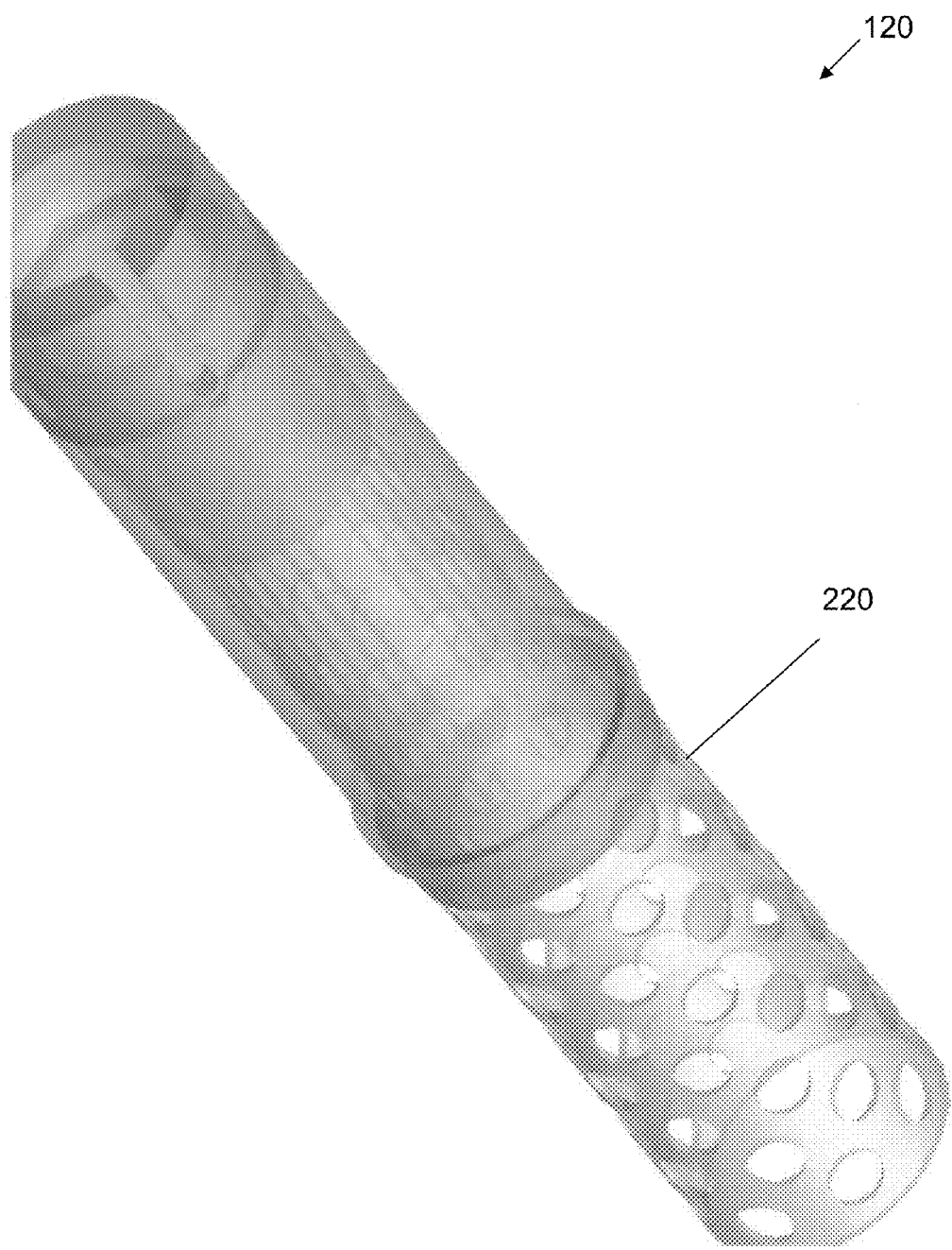
FIG. 21 is a diagrammatic representation of a cut away perspective view of a representative proximal portion of a device.

Conductors 230, 230A, 230B, 230C and shielding member 250 are shown in FIG. 20. Referring to FIG. 21, a diagrammatic representation of a cut away perspective view of a representative proximal portion of a device 120 is shown. Reinforcement member 220 in the embodiment shown in FIG. 20 is a perforated tube.

Devices as described herein may be made according to any known or future developed process. For example, the body material of devices may be injection molded or extruded. In some situations it may be desirable to reflow body material from thermoplastic polymers. Body material is typically made of polymeric material, such as polyurethane, polycarbonate, or silicone or combinations thereof. Body material typically has an elastic modulus of less than 15 ksi (less than 100 MPa), e.g. between 0.5 and 5 ksi (between 3.5 and 35 MPa).

Reinforcement member may be extruded, molded, or the like. Reinforcement member may be made of any material that can increase the tensile strength of body of device when reinforcement member is integrated into body. By way of example, reinforcement member may have an elastic modulus of 5 times or greater, 10 times or greater, 25 times or greater, 50 times or greater, or 100 times or greater than the elastic modulus of body material. In various embodiments, the elastic modulus of reinforcement member is 200 ksi (1400 MPa) or greater, 300 ksi (2100 MPa) or greater, 400 ksi (2800 MPa) or greater, 500 ksi (3500 MPa) or greater, or between 200 ksi (1400 MPa) and 1000 ksi (7000 mPa). When reinforcement member is connected to contact, it is desirable that reinforcement member be non-conductive. Exemplary non-conductive materials for use as reinforcement member include ceramic materials or polyester polymeric materials, such as polyethylene naphthalate, polyethylene terephthalate, polyether ether ketone, polyetherether ketone or the like.

Electrodes may be formed of electrically conductive biocompatible materials, such as platinum or platinum iridium. Contacts and conductors may be formed of electrically conductive biocompatible materials, such as platinum, platinum iridium, titanium, tantalum, nickel-cobalt-chromium-molybdenum alloys, or the like. Conductors may comprise braided strand wire.

Shielding member may be as described in US Patent Application Publication No. 2005/0222658.

One exemplary way to make a device having a reinforcing member integrated into the body of the device is: capture reinforcing mesh or braid in connector ring (e.g., as discussed with regard to FIG. 20); dispose reinforcing mesh or braid over shielding member, which is disposed on polyurethane tubing; place outer polyurethane tubing over reinforcing mesh; place shrink tubing (e.g., polytetrafluoroethylene or fluorinated ethylene-propylene) over outer polyurethane tubing; heat to reflow polyurethane with shrink tubing serving to ensure proper contacting and bonding of polyurethane. Otherwise, device may be made as is known in the art for leads, lead extensions, and the like. Of course, any suitable method may be used to make a device as described herein.

Thus, embodiments of the LEAD HAVING REINFORCING MEMBER are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device that operably couples to an apparatus for delivery electrical signals in a patient, the implantable medical device comprising:
    a body comprising:
        (i) a proximal end portion configured to be at least partially received by the apparatus, and
        (ii) a distal end portion, the body comprising a polymeric material;
    a conductive member at the distal end portion of the body;
    an electrical contact at the proximal end portion of the body, the electrical contact being electrically coupled to the conductive member by a conductor and being positioned such that, when received by the apparatus, at least a portion of the apparatus is capable of electrically coupling to the electrical contact; and
    a reinforcement member integrated into the polymeric material of the body, the reinforcement member in contact with the electrical contact and extending distally within the polymeric material of the body from the electrical contact,
    wherein, the electrical contact is configured to receive a compressive force from the apparatus when the proximal end portion of the body is received by the apparatus, the reinforcement member is located in the body at a point configured to receive the compressive force, the implantable medical device is configured to be secured to the apparatus by the compressive force, and the implantable medical device is configured such that a tensile load on the polymeric material of the body is transferred to the reinforcement member along where the reinforcement member is integrated into the polymeric material of the body when a pull force is placed on the body.

2. The implantable medical device of claim 1, wherein, when the proximal end portion is received by the apparatus, the compressive force applied to the body results in a retention force of 1.5 pounds or greater.

3. The implantable medical device of claim 1, wherein the reinforcement member provides the body with tensile strength with minimal elongation to withstand an average pull force of 2 pounds or greater, the pull force being applied at a location distal the location to which the compressive force is applied.

4. The implantable medical device of claim 1 wherein the electrical contact is configured to receive the compressive force from a set screw of the apparatus to secure the implantable medical device to the apparatus.

5. The implantable medical device of claim 1, wherein the reinforcement member extends in the body from an area to be received by the apparatus to a location distal the area to be received by the apparatus.

6. The implantable medical device of claim 1, wherein the electrical contact comprises a first part having an outer surface and a second part having an inner surface, at least a portion of the inner surface of the second part being complementarily configured relative to at least a portion of the outer surface of the first part, and
    wherein at least a portion of the reinforcing member is disposed between the first and second parts of the contact.

7. The implantable medical device of claim 6, wherein the first part of the electrical contact is electrically coupled to the second part of the electrical contact.

8. The implantable medical device of claim 1, wherein the reinforcing member comprises a rod, the rod being connected to the electrical contact via a cross member.

9. The implantable medical device of claim 1, wherein the reinforcement member comprises a mesh, braid, or perforated tube.

10. The implantable medical device of claim 1, wherein the reinforcing member comprises polyethylene naphthalate, polyethylene terephthalate, or polyetherether ketone.

11. The implantable medical device of claim 1, wherein the reinforcing member has an elastic modulus of 200 ksi or greater.

12. The implantable medical device of claim 1, wherein the reinforcement member is integrated into the polymeric material of the body at a location to resist the polymeric material from pulling away from the electrical contact by the pull force.

13. The implantable medical device of claim 1, further comprising a shielding member disposed between at least a portion of the reinforcing member and at least a portion of the conductive member.

14. The implantable medical device of claim 1, further comprising a shielding member having a lumen, wherein at least a portion of the reinforcing member and at least a portion of the conductive member are disposed within the lumen of the shielding member.

15. The implantable medical device of claim 1, wherein the conductive member is an electrode.

16. The implantable medical device of claim 1, wherein the implantable medical device is a lead.

17. The implantable medical device of claim 1, wherein the implantable medical device is a lead extension.

18. The implantable medical device of claim 1, wherein the implantable medical device is an adapter configured to couple a lead or lead extension to an implantable signal generator.

19. A system comprising:
    the implantable medical device of claim 1, and
    the apparatus by which the device of claim 1 is configured to be received.

20. The system of claim 19, wherein the implantable medical device is a lead and the apparatus is a lead extension.

21. The system of claim 19, wherein the implantable medical device is a lead and the apparatus is an implantable signal generator.

* * * * *